(12) United States Patent
Bodashefsky et al.

(10) Patent No.: US 10,631,944 B2
(45) Date of Patent: Apr. 28, 2020

(54) OROPHARYNGEAL MEASUREMENT DEVICE AND METHOD

(71) Applicants: Brock Bodashefsky, Newcastle (CA); Douglas Bird, Newcastle (CA)

(72) Inventors: Brock Bodashefsky, Newcastle (CA); Douglas Bird, Newcastle (CA)

(*) Notice: Subject to any disclaimer, the term of this patent is extended or adjusted under 35 U.S.C. 154(b) by 391 days.

(21) Appl. No.: 15/795,058

(22) Filed: Oct. 26, 2017

(65) Prior Publication Data

US 2019/0125478 A1 May 2, 2019

(51) Int. Cl.
*A61B 5/107* (2006.01)
*A61B 90/00* (2016.01)
*A61M 16/00* (2006.01)
*A61M 16/04* (2006.01)

(52) U.S. Cl.
CPC ............ *A61B 90/06* (2016.02); *A61B 5/1072* (2013.01); *A61M 16/0003* (2014.02); *A61M 16/04* (2013.01); *A61B 2090/061* (2016.02); *A61M 2205/3327* (2013.01)

(58) Field of Classification Search
CPC ..................................................... A61B 90/06
USPC ........................................................... 33/512
See application file for complete search history.

(56) References Cited

U.S. PATENT DOCUMENTS

| | | | | |
|---|---|---|---|---|
| 3,643,651 A | * | 2/1972 | Cuadros | A61B 5/1076 600/591 |
| 4,690,138 A | * | 9/1987 | Heyden | A61M 16/04 116/324 |
| 4,940,063 A | * | 7/1990 | Challis | A61B 5/1071 33/512 |
| 5,297,346 A | * | 3/1994 | Weiner | A61B 5/1076 33/512 |
| 5,957,134 A | * | 9/1999 | Lee | A61M 16/04 128/207.14 |
| 6,159,167 A | * | 12/2000 | Hardin-Naser | A61B 5/107 33/512 |
| 6,626,169 B2 | | 9/2003 | Gaitini | |
| 7,036,501 B2 | | 5/2006 | Wall | |
| 7,607,238 B2 | * | 10/2009 | Kim | G01B 3/28 33/512 |
| 7,866,313 B2 | | 1/2011 | Isenberg et al. | |
| 8,366,640 B2 | * | 2/2013 | Bauer | A61B 5/1076 600/591 |
| 8,371,291 B2 | * | 2/2013 | Haroutunian | A61M 15/0086 128/200.14 |

(Continued)

FOREIGN PATENT DOCUMENTS

| | | |
|---|---|---|
| EP | 1477198 | 4/2007 |
| EP | 2992919 | 3/2016 |

*Primary Examiner* — George B Bennett
(74) *Attorney, Agent, or Firm* — Oyen Wiggs Green & Mutala LLP

(57) ABSTRACT

An oropharyngeal measurement device includes a tubular body, a sealed channel, a radial flange member, and a measurement indicator on the outer surface of the tubular body. The tubular body includes a proximal end and a distal end. The sealed channel extends within the tubular body from the proximal end to the distal end and includes a plurality of bends configured to conform with the airway of a user. The measurement indicator is useful for placing alongside the face of a patient from the mouth towards the throat, in order to gauge an approximation for a oropharyngeal airway device to be used during a medical procedure.

20 Claims, 5 Drawing Sheets

(56) References Cited

U.S. PATENT DOCUMENTS

| | | | |
|---|---|---|---|
| 9,357,905 B2 * | 6/2016 | Molnar | A61M 16/04 |
| 9,415,179 B2 * | 8/2016 | Molnar | A61B 7/003 |
| 2001/0032646 A1 * | 10/2001 | Christopher | A61M 16/0488 128/200.26 |
| 2001/0054425 A1 * | 12/2001 | Bertram | A61M 16/04 128/207.15 |
| 2002/0104230 A1 * | 8/2002 | White | G01B 3/28 33/755 |
| 2003/0131853 A1 | 7/2003 | Wall | |
| 2005/0066535 A1 * | 3/2005 | Rupp | A61B 5/1072 33/512 |
| 2006/0207118 A1 * | 9/2006 | Kim | A61B 5/1076 33/512 |

* cited by examiner

OROPHARYNGEAL MEASUREMENT DEVICE AND METHOD

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of surgical devices of existing art and more specifically relates to an oropharyngeal measurement device.

RELATED ART

Respiratory aids include tubular devices that are inserted into a patient's body so as to provide an airway through which the patient can breathe. One such device is a so-called Guedel or oropharyngeal airway which includes a curved tube that is inserted into a patient's mouth and extends, once inserted, into the oropharynx. A Guedel airway prevents the tongue and epiglottis from falling backwards, and also prevents the pharynx collapsing following anaesthesia, thereby maintaining the patency of the upper airway of an unintubated patient.

Guedel airways are designed in different sizes to fit patients from neonatals to adults. They consist of a curved air channel that is flattened anteroposteriorly and curved laterally (arched). A protective flange at the oral end is provided to ensure that the device is secure in use, and does not slip into the oral cavity. The portion that fits between the teeth is typically made of hardened plastic to ensure that the air channel is not occluded if the patient bites down on the airway. An additional hardened plastic insert is typically used to add strength, and this insert is often colour-coded to denote the size of the airway. With many surgical procedures, time is of the essence. Often times, precious seconds and incorrectly sized equipment can be wasted when trying to place an incorrectly sized airway device in a patient. A suitable solution is desired.

U.S. Pat. No. 2003/0131853 to William Wall relates to an oro-pharyngeal airway and gas-assisted injection molding method therefor. The described oro-pharyngeal airway and gas-assisted injection molding method therefor includes an oro-pharyngeal apparatus defining both a suction conduit adapted to receive an operative connection to a suction pump for removing liquids from a patient's throat and at least one airway through which the patient can breathe during medical or dental treatment. The invention allows simultaneous use of the suction conduit and airway. Alternately, an oxygen pump can be connected to the conduit for insufflation of the patient. The airway is provided with a color-coded ring to indicate a pre-determined size of the airway to accommodate various sized individuals. The device is fabricated by gas assisted injection molding techniques.

SUMMARY OF THE INVENTION

In view of the foregoing disadvantages inherent in the known surgical devices art, the present disclosure provides a novel oropharyngeal measurement device. The general purpose of the present disclosure, which will be described subsequently in greater detail, is to provide a color-coded guide for visually estimating the size of oropharyngeal airway to be used on a patient.

An oropharyngeal measurement device is disclosed herein. The oropharyngeal measurement device may include a tubular body, a sealed channel, a radial flange member, and a measurement indicator on the outer surface of the tubular body. The tubular body may include a proximal end and a distal end. The sealed channel may extend within the tubular body from the proximal end to the distal end and may include a plurality of bends configured to conform with the airway of a user. The measurement indicator may be useful for placing alongside the face of a patient from the mouth towards the throat, in order to gauge an approximation for an oropharyngeal airway device to be used.

According to another embodiment, a method for using an oropharyngeal measurement device is also disclosed herein. The method for using an oropharyngeal measurement device includes providing an oropharyngeal measurement device, holding the oropharyngeal measurement device alongside a face of a user, and identifying an appropriate length for an oropharyngeal airway device based upon the measurement indicator.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, an oropharyngeal measurement device, constructed and operative according to the teachings of the present disclosure.

DETAILED DESCRIPTION

As discussed above, embodiments of the present disclosure relate to a surgical device and more particularly to an oropharyngeal measurement device as used to provide a color-coded guide for visually estimating the size of an oropharyngeal airway to be used on a patient.

Generally, the oropharyngeal measurement device may include a measuring guide that may allow anyone to quickly, and accurately, measure a patient for an oral pharyngeal airway. The device may be configured as a tubular body having a sealed channel, a radial flange member, and a measurement indicator on the outer surface of the tubular body. The tubular body may include a proximal end and a distal end. The sealed channel may extend within the tubular body from the proximal end to the distal end and may include a plurality of bends configured to conform to the airway of a user. The measurement indicator may be useful for placing alongside the face of a patient from the mouth towards the throat, in order to gauge an approximation for an oropharyngeal airway device to be used.

The oropharyngeal measurement device of this disclosure resembles the configuration of an oropharyngeal airway device, but may not include a central air hole so as to not be confused with a functional oropharyngeal airway device. Traditionally, to measure an oropharyngeal airway, a technician may guestimate the size, take the oropharyngeal airway device from the package, and then measure from the corner of the mouth to the earlobe. The oropharyngeal measurement device may allow for the rapid, and accurate, measurement for the proper size. This may reduce time and save on wasted, miss-sized airways. The measuring technique is currently from ear lobe to corner of the mouth but the user may also do it from mouth to ear.

The oropharyngeal measurement device may include a plurality of color coded bars or stripes along the long axis of the device. This color-coding system may correspond to oropharyngeal airway devices, thereby making it quicker and easier to select the proper sizing for a patient. The oropharyngeal measurement device may be configured in a variety of dimensions and sizes ranging from approximately 30 mm, up to over 110 mm. The device may be constructed as a lightweight, one-piece instrument that allows for easy transportation and carry of the device. The device may allow a medical technician or user to take measurements in multiple ways including: visually approximations using the included color code; traditional imperial or metric markings; and/or sizing numbers. The colors for the color codes may encircle the device with the size (in units) on one side and a size number on the other.

Referring now more specifically to the drawings by numerals of reference, there is shown in FIGS. 1-4, various views of an oropharyngeal measurement device 100.

Figure 1:
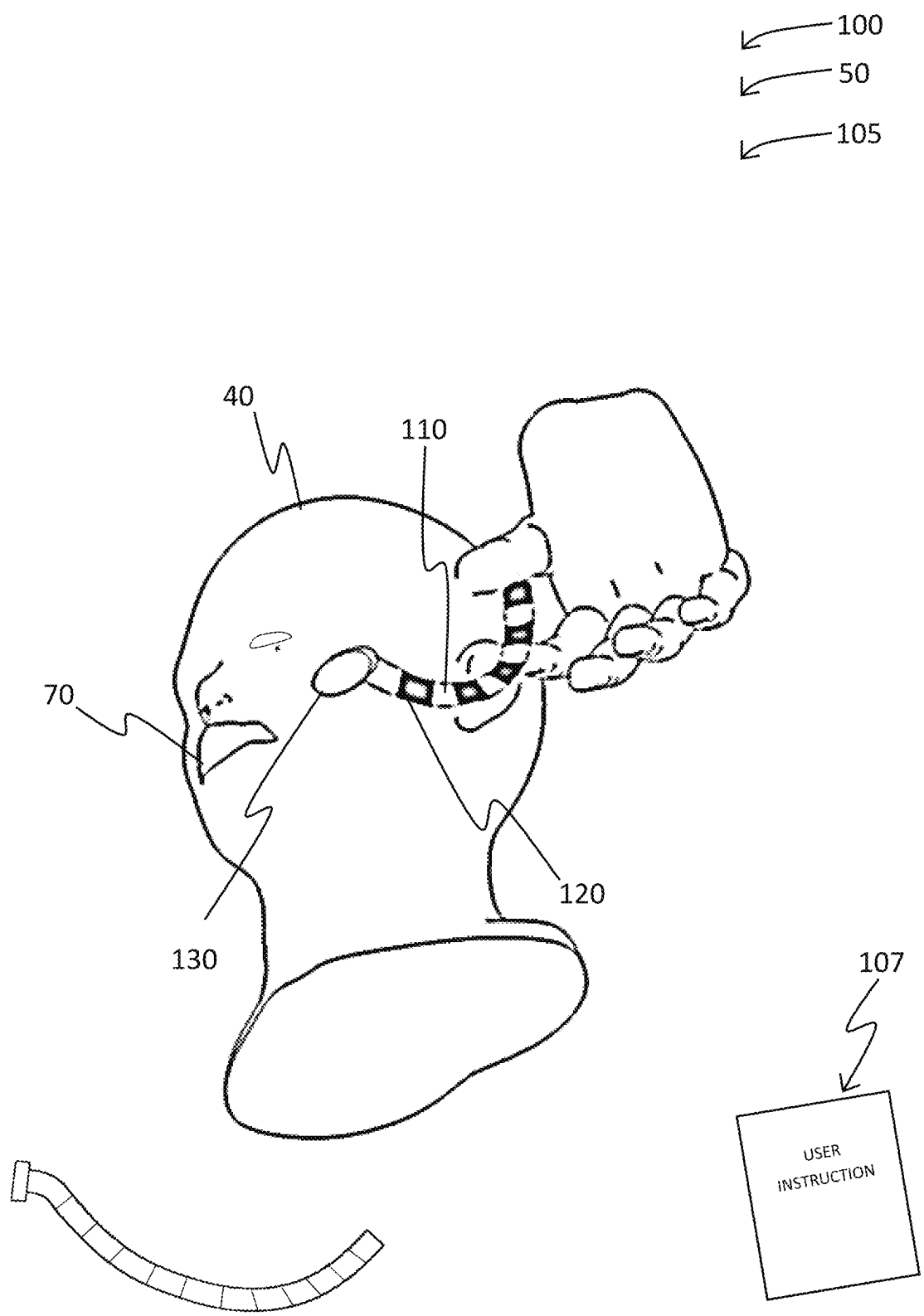
FIG. 1 is a perspective view of the oropharyngeal measurement device during an 'in-use' condition, according to an embodiment of the disclosure.

FIG. 1 shows an oropharyngeal measurement device 100 during an 'in-use' condition 50, according to an embodiment of the present disclosure. Here, the oropharyngeal measurement device 100 may be beneficial for use by a user 40 to provide a color-coded guide for visually estimating the size of an oropharyngeal airway to be used on a patient. As illustrated, the oropharyngeal measurement device 100 may include a tubular body 110, a sealed channel 120 extending within the tubular body 110, a radial flange member 130 configured to locate adjacent to an outer region of a mouth of the user 40 in order to estimate the size of the airway 70.

According to one embodiment, the oropharyngeal measurement device 100 may be arranged as a kit 105. In particular, the oropharyngeal measurement device 100 may further include a set of instructions 107. The instructions 107 may detail functional relationships in relation to the structure of the oropharyngeal measurement device 100 such that the oropharyngeal measurement device 100 can be used, maintained, or the like, in a preferred manner.

Figure 2:
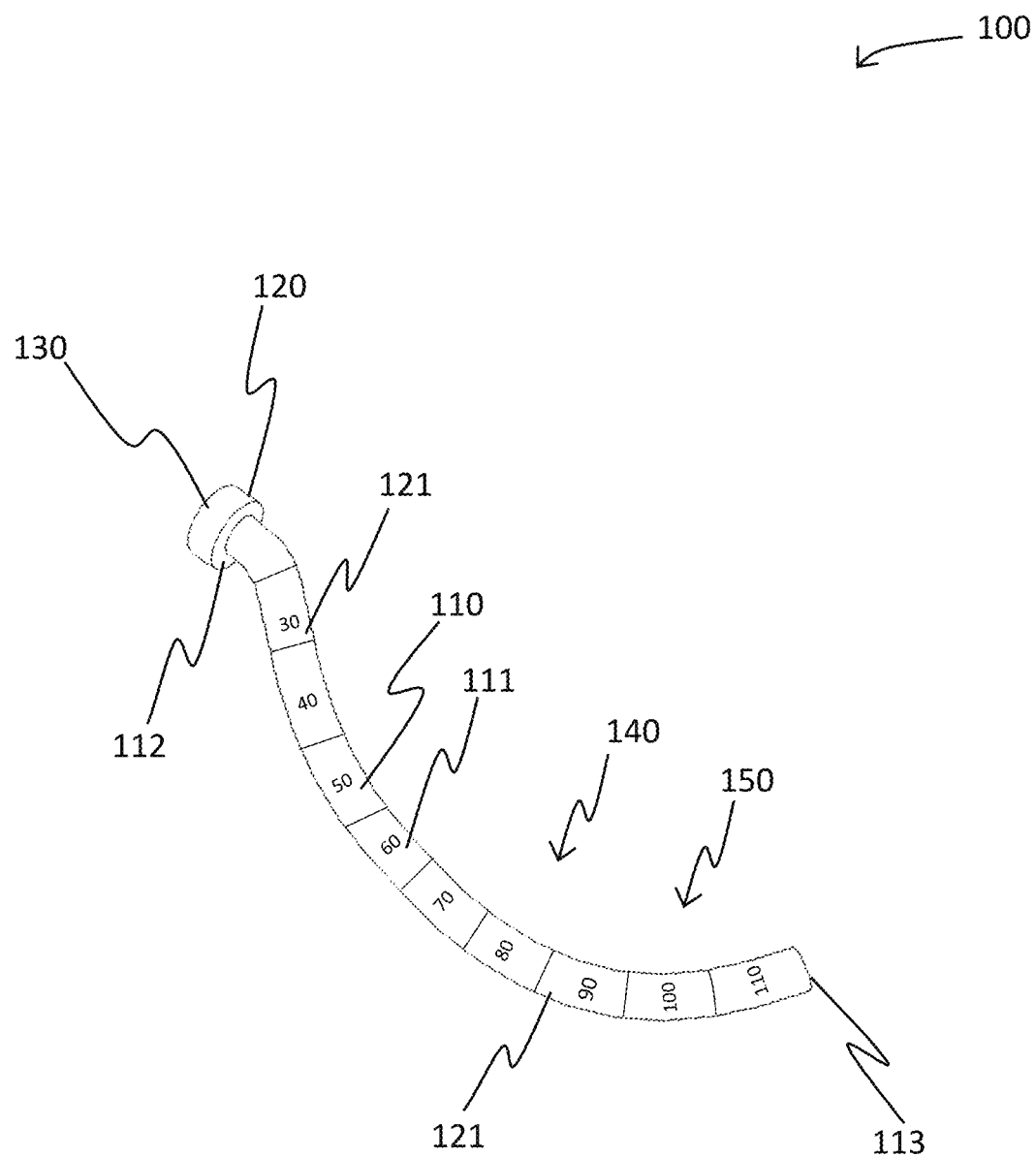
FIG. 2 is a side view of the oropharyngeal measurement device of FIG. 1 showing a tubular body and sealed channel with a measurement indicator for estimating an oropharyngeal airway device, according to an embodiment of the present disclosure.

FIG. 2 shows the oropharyngeal measurement device 100 of FIG. 1, according to an embodiment of the present disclosure. As above, the oropharyngeal measurement device 100 may include a tubular body 110 having an outer surface 111, a proximal end 112 and a distal end 113. The device may further include a sealed channel 120 extending within the tubular body 110 from the proximal end 112 to the distal end 113 of the tubular body 110, the sealed channel 120 including a plurality of bends 121 configured to conform with an airway 70 (see FIG. 1) of a user 40 (not pictured). The oropharyngeal measurement device 100 may also include a measurement indicator 140 on the outer surface 111 of the tubular body 110 for holding next to the face of a user 40 (not pictured) and estimating the size of the airway 70 (see FIG. 1). The measurement indicator 140 may further comprise functional indicia 150 for estimating a measurement. Additionally, the device may feature a radial flange member 130 fixed to the proximal end 112 of the tubular body 110.

Figure 3:
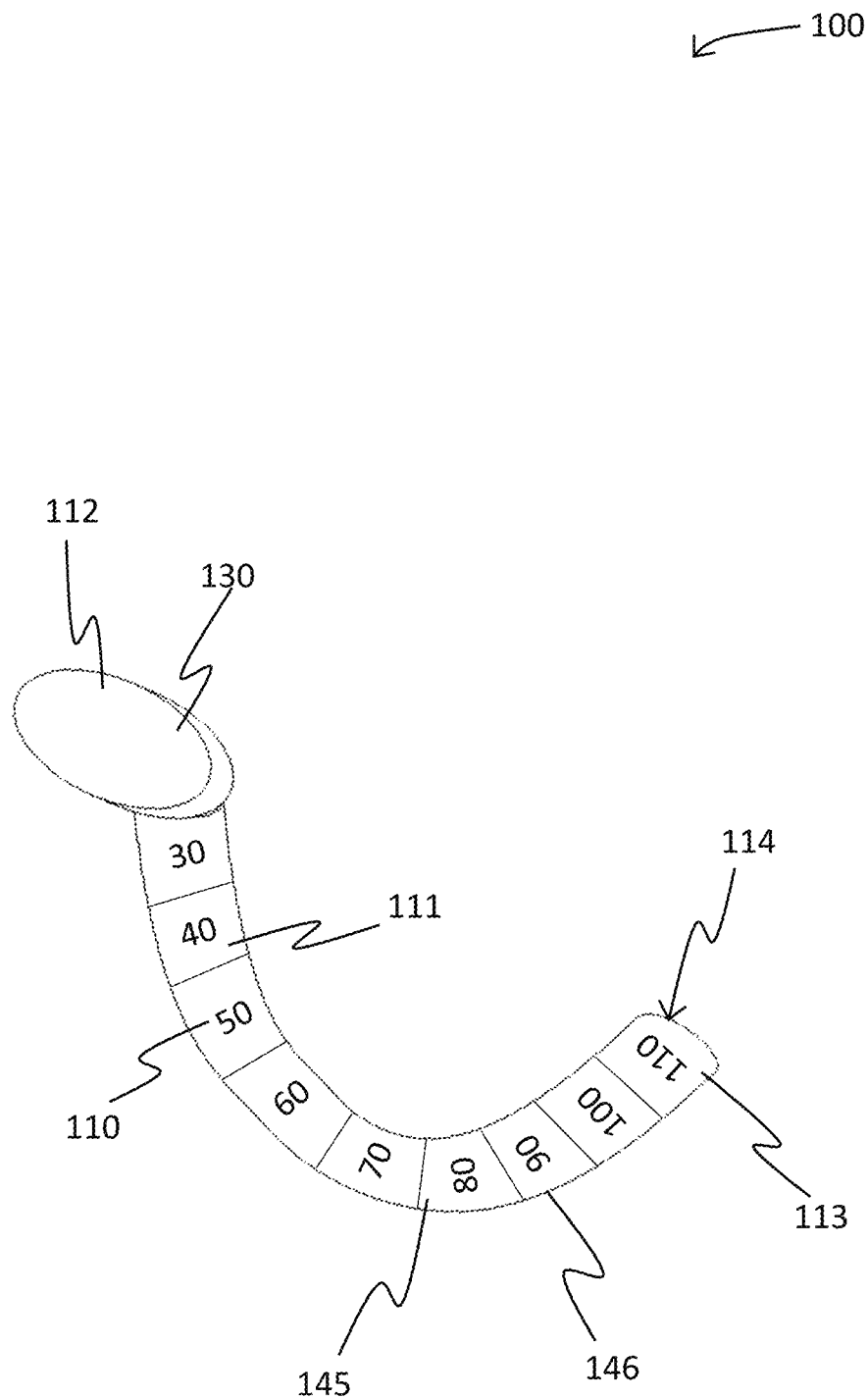
FIG. 3 is another perspective view of the oropharyngeal measurement device of FIG. 1, according to an embodiment of the present disclosure.

FIG. 3 is a perspective view of the oropharyngeal measurement device 100 of FIG. 1, according to an embodiment of the present disclosure. As above, the oropharyngeal measurement device 100 may include a tubular body 110 having an outer surface 111, a proximal end 112 and a distal end 113 including a rounded edge 114. The oropharyngeal measurement device 100 may also have a radial flange member 130 fixed to the proximal end 112 of the tubular body 110. The tubular body 110 of the oropharyngeal measurement device 100 may feature a plurality of stripes 145 including a color code 146 for making quick and easy visual estimates to the size of airway 70 (see FIG. 1) of a user 40 (not shown).

Figure 4:
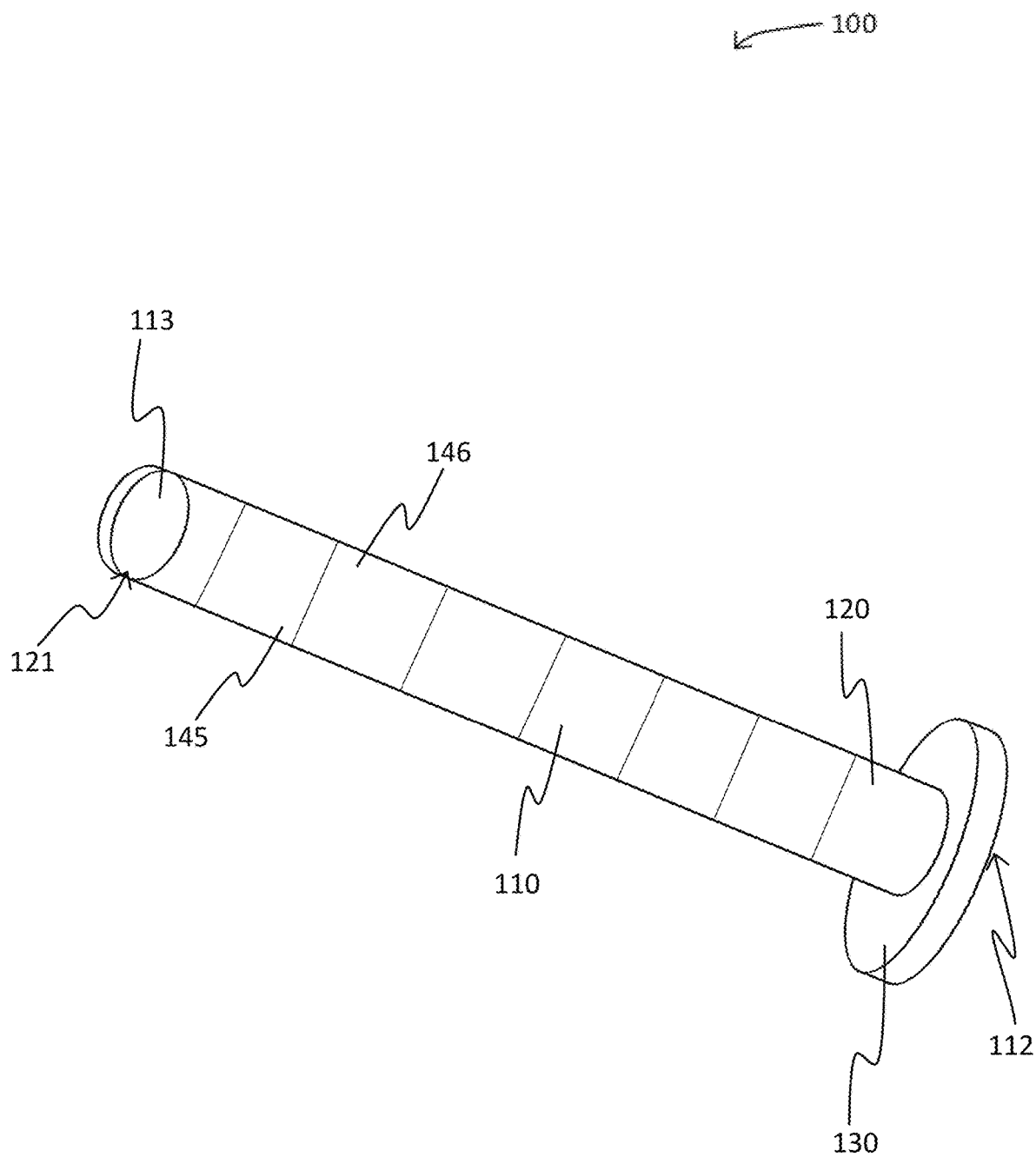
FIG. 4 is a top perspective view of the oropharyngeal measurement device of FIG. 1, according to an embodiment of the present disclosure.

FIG. 4 is a top perspective view of the oropharyngeal measurement device 100 of FIG. 1, according to an embodiment of the present disclosure. Here again, the oropharyngeal measurement device 100 may include a tubular body 110 having a proximal end 112 and a distal end 113. The oropharyngeal measurement device 100 may also include a sealed channel 120 including a plurality of bends 121 extending within the tubular body 110 from the proximal end 112 to the distal end 113 of the tubular body 110. Further still, the oropharyngeal measurement device 100 may include a radial flange member 130 fixed to the proximal end 112 of the tubular body 110 to provide a gripping surface. Again still, the tubular body 110 of the oropharyngeal measurement device 100 may feature a plurality of stripes 145 including a color code 146 for making estimated measurements.

Figure 5:
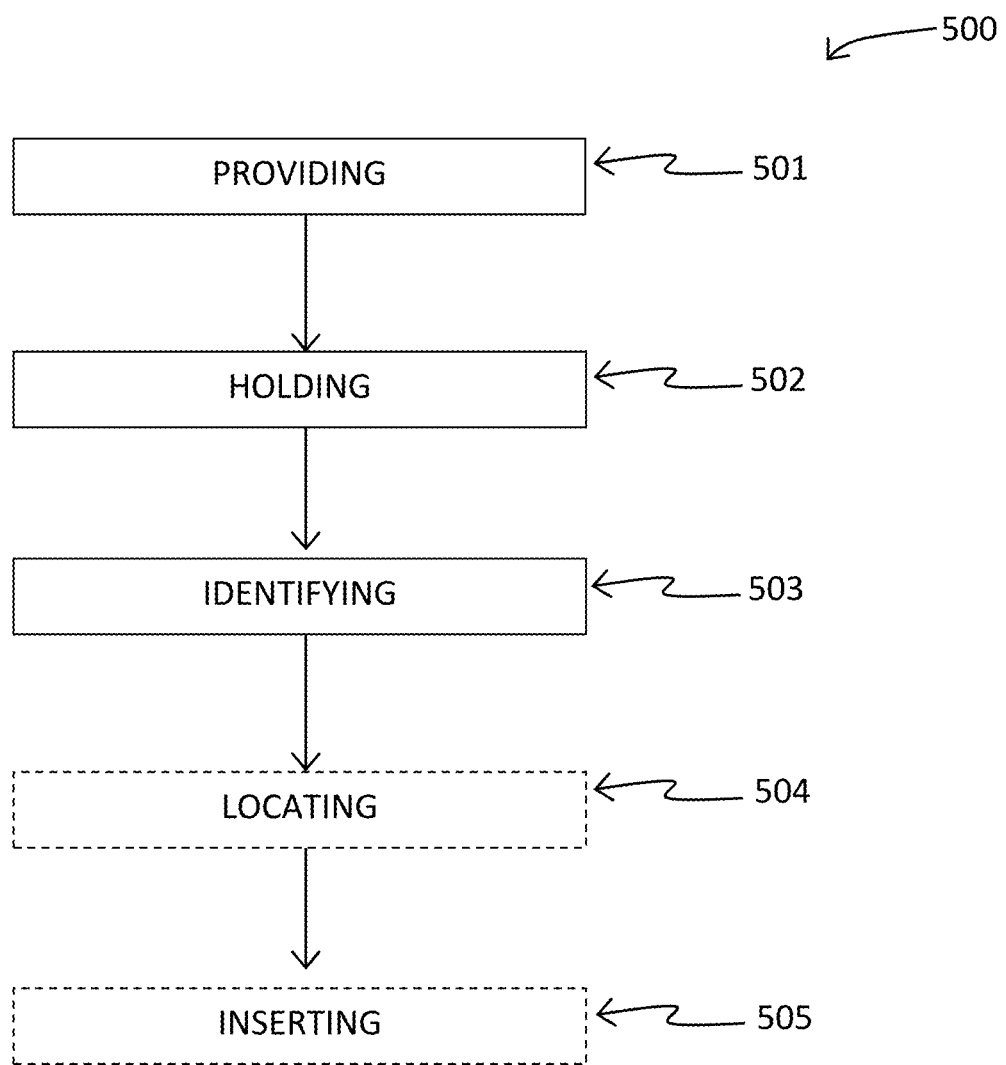
FIG. 5 is a flow diagram illustrating a method for using the oropharyngeal measurement device, according to an embodiment of the present disclosure.

FIG. 5 is a flow diagram illustrating a method for using 500 the oropharyngeal measurement device 100, according to an embodiment of the present disclosure. In particular, the method for using 500 may include one or more components or features of the oropharyngeal measurement device 100 as described above. As illustrated, the method for using 500 the oropharyngeal measurement device 100 may include the steps of: step one 501, providing an oropharyngeal measurement device 100 including a tubular body 110 having an outer surface 111 a proximal end 112 and a distal end 113, a sealed channel 120 extending within the tubular body 110 from the proximal end 112 to the distal end 113 of the tubular body 110, a radial flange member 130 fixed to the proximal end 112 of the tubular body 110, and a measurement indicator 140 on the outer surface 111 of the tubular body 110; step two 502, holding the oropharyngeal measurement device 100 alongside a face of a user 40, the device positioned with the radial flange approximate the user's 40 mouth; and step three 503, identifying an appropriate length for an oropharyngeal airway device based upon the measurement indicator 140.

It should be noted that step four 504 and step five 505 are optional steps and may not be implemented in all cases. Optional steps of method of use 500 are illustrated using dotted lines in FIG. 5 so as to distinguish them from the other steps of method of use 500. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for oropharyngeal measurement device 100 are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. An oropharyngeal measurement device comprising:
    a tubular body having an outer surface, a proximal end and a distal end;
    a sealed channel extending within the tubular body from the proximal end to the distal end of the tubular body, the sealed channel including a plurality of bends configured to conform with an airway of a user;
    a radial flange member fixed to the proximal end of the tubular body, the radial flange member configured to locate adjacent to an outer surface of a mouth of the user; and
    a measurement indicator on the outer surface of the tubular body.

2. The oropharyngeal measurement device of claim 1, wherein the measurement indicator comprises a plurality of stripes.

3. The oropharyngeal measurement device of claim 2, wherein each of the plurality of stripes is equal in width.

4. The oropharyngeal measurement device of claim 2, wherein each of the plurality of stripes is perpendicular in relation to the tubular body.

5. The oropharyngeal measurement device of claim 2, wherein each of the plurality of stripes includes a color code.

6. The oropharyngeal measurement device of claim 2, wherein the plurality of stripes circumscribes the tubular body.

7. The oropharyngeal measurement device of claim 5, wherein the color code of each stripe is non-repeating on the tubular body.

8. The oropharyngeal measurement device of claim 5, wherein the color code of each stripe is configured to represent a length for selecting an oropharyngeal airway device.

9. The oropharyngeal measurement device of claim 1, wherein the measurement indicator further comprises functional indicia.

10. The oropharyngeal measurement device of claim 9, wherein the functional indicia includes a measurement guide.

11. The oropharyngeal measurement device of claim 1, wherein the distal end includes a rounded edge.

12. The oropharyngeal measurement device of claim 1, wherein the tubular body tapers in diameter from the proximal end to the distal end.

13. The oropharyngeal measurement device of claim 1, wherein the device weighs less than 2 lbs.

14. The oropharyngeal measurement device of claim 1, wherein the tubular body is generally elliptical when viewed in transverse cross-section.

15. The oropharyngeal measurement device of claim 1, wherein the device comprises rubber.

16. The oropharyngeal measurement device of claim 1, wherein the device comprises plastic.

17. An oropharyngeal measurement device comprising:
    a tubular body having an outer surface, a proximal end and a distal end;
    a sealed channel extending within the tubular body from the proximal end to the distal end of the tubular body, the sealed channel including a plurality of bends configured to conform with an airway of a user;
    a radial flange member fixed to the proximal end of the tubular body, the radial flange member configured to locate adjacent to an outer surface of a mouth of the user; and
    a measurement indicator on the outer surface of the tubular body;
    wherein the measurement indicator comprises a plurality of stripes;
    wherein each of the plurality of stripes is equal in width;
    wherein each of the plurality of stripes is perpendicular in relation to the tubular body;
    wherein each of the plurality of stripes includes a color code;
    wherein the plurality of stripes circumscribes the tubular body;
    wherein the color code of each stripe is non-repeating on the tubular body;
    wherein the color code of each stripe is configured to represent a length for selecting an oropharyngeal airway device;
    wherein the measurement indicator further comprises functional indicia;
    wherein the functional indicia includes a measurement guide;
    wherein the distal end includes a rounded edge;
    wherein the tubular body tapers in diameter from the proximal end to the distal end;
    wherein the device weighs less than 2 lbs;
    wherein the tubular body is generally elliptical when viewed in transverse cross-section;
    wherein the device comprises rubber;
    wherein the device comprises plastic.

18. The oropharyngeal measurement device of claim 17, further comprising set of instructions; and
wherein the device is arranged as a kit.

19. A method for using an oropharyngeal measurement device, the method comprising the steps of:
provide an oropharyngeal measurement device including a tubular body having an outer surface a proximal end and a distal end, a sealed channel extending within the tubular body from the proximal end to the distal end of the tubular body, a radial flange member fixed to the proximal end of the tubular body, and a measurement indicator on the outer surface of the tubular body;
holding the oropharyngeal measurement device alongside a face of a user, the device positioned with the radial flange approximate the user's mouth; and
identifying an appropriate length for an oropharyngeal airway device based upon the measurement indicator.

20. The method of claim 19, further comprising the steps of:
locating an oropharyngeal airway device that corresponds in dimensions to the appropriate length identified with the measurement indicator of the oropharyngeal measurement device; and
inserting the selected oropharyngeal airway device into the airway of the user.

* * * * *